United States Patent
Takahashi

(10) Patent No.: US 9,099,931 B2
(45) Date of Patent: Aug. 4, 2015

(54) POWER SUPPLY DEVICE

(71) Applicant: OLYMPUS CORPORATION, Tokyo (JP)

(72) Inventor: Hajime Takahashi, Inagi (JP)

(73) Assignee: OLYMPUS CORPORATION, Tokyo (JP)

( * ) Notice: Subject to any disclaimer, the term of this patent is extended or adjusted under 35 U.S.C. 154(b) by 107 days.

(21) Appl. No.: 13/932,405

(22) Filed: Jul. 1, 2013

(65) Prior Publication Data

US 2013/0294122 A1 Nov. 7, 2013

Related U.S. Application Data

(63) Continuation of application No. PCT/JP2011/078573, filed on Dec. 9, 2011.

(30) Foreign Application Priority Data

Jan. 20, 2011 (JP) ................. 2011-010128

(51) Int. Cl.
*H02H 7/125* (2006.01)
*H02M 1/36* (2007.01)
*H02M 7/217* (2006.01)
*G06F 1/30* (2006.01)

(52) U.S. Cl.
CPC . *H02M 1/36* (2013.01); *G06F 1/30* (2013.01); *H02M 7/217* (2013.01); *A61B 2560/0214* (2013.01)

(58) Field of Classification Search
CPC ................................ H02M 1/36; H02M 7/217
USPC ................................ 363/50, 52, 53
See application file for complete search history.

(56) References Cited

U.S. PATENT DOCUMENTS

| | | | |
|---|---|---|---|
| 6,111,764 A * | 8/2000 | Atou et al. | 363/37 |
| 6,212,081 B1 * | 4/2001 | Sakai | 363/71 |
| 7,054,169 B2 * | 5/2006 | Huh et al. | 363/21.16 |
| 2010/0022828 A1 | 1/2010 | Ono et al. | |
| 2010/0246226 A1 * | 9/2010 | Ku et al. | 363/126 |

FOREIGN PATENT DOCUMENTS

| | | |
|---|---|---|
| EP | 1 889 565 A1 | 2/2008 |
| JP | 04-031772 A | 2/1992 |
| JP | 09-068548 A | 3/1997 |
| JP | 2006-340921 A | 12/2006 |
| WO | WO 2006/132323 A1 | 12/2006 |

OTHER PUBLICATIONS

International Search Report dated Feb. 21, 2012 issued in PCT/JP2011/078573.

* cited by examiner

*Primary Examiner* — Matthew Nguyen
(74) *Attorney, Agent, or Firm* — Scully, Scott, Murphy & Presser, PC

(57) ABSTRACT

A power supply device includes a converter, a rectifier circuit, a voltage cycle detection circuit, and a power supply cutoff signal output unit. The converter converts an AC voltage inputted from an external power supply to a DC voltage and outputs the DC voltage. The rectifier circuit rectifies the AC voltage inputted from the external power supply and outputs a rectified waveform voltage. The voltage cycle detection circuit detects a voltage cycle in which the rectified waveform voltage reaches a predetermined threshold value and, when the voltage cycle is detected to be longer than a predetermined cycle, outputs a voltage cycle abnormality signal. The power supply cutoff signal output unit outputs a power supply cutoff signal when the voltage cycle abnormality signal is inputted.

2 Claims, 7 Drawing Sheets

| INPUT | | OUTPUT |
|---|---|---|
| POINT C | POINT D | OFF SIGNAL |
| LOW | LOW | HIGH |
| LOW | HIGH | LOW |
| HIGH | LOW | LOW |

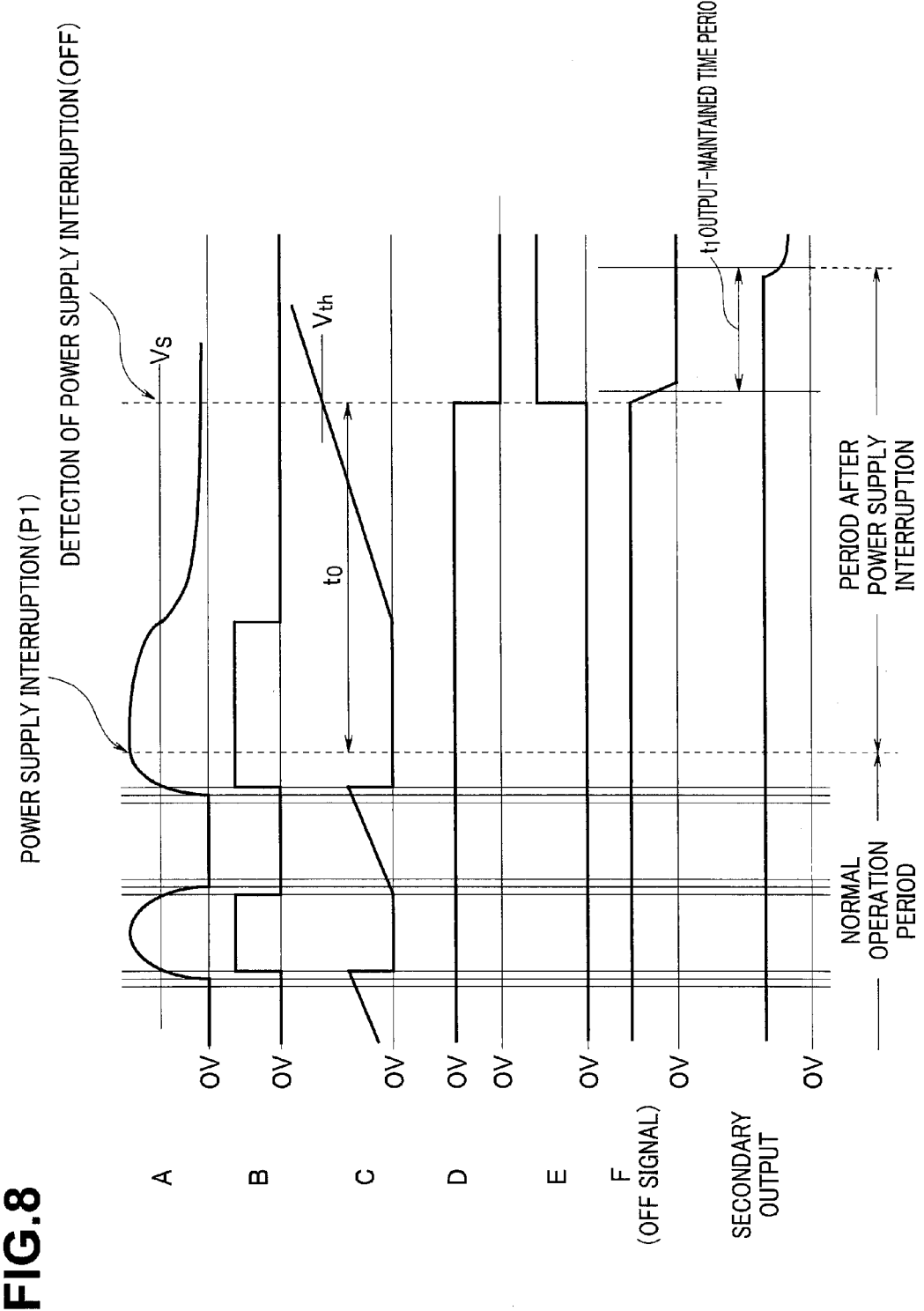

US 9,099,931 B2

POWER SUPPLY DEVICE

CROSS REFERENCE TO RELATED APPLICATION

This application is a continuation application of PCT/JP2011/078573 filed on Dec. 9, 2011 and claims benefit of Japanese Application No. 2011-010128 filed in Japan on Jan. 20, 2011, the entire contents of which are incorporated herein by this reference.

BACKGROUND OF THE INVENTION

1. Field of the Invention

The present invention relates to a power supply device and, more particularly, to a power supply device which can reliably perform data preservation even in the event of an unexpected power supply interruption in a medical device.

2. Description of the Related Art

It is necessary for a medical device to reliably preserve data obtained so far on a side of a product circuit (e.g., a processor) if supply of power to the device is interrupted.

For example, Japanese Patent Application Laid-Open Publication No. 2006-340921 proposes a technique in which turning off of a power switch triggers a process for an image pickup device, a display device, and the like of outputting an interruption signal for immediate stopping of power supply and a process for a processor of continuing supply of power to the processor for a fixed time period by generating an interruption signal which is delayed by the fixed time period in order to reliably implement data preservation at the time of a power supply interruption and interrupting the supply of power to the processor after a lapse of the fixed time period, when a power supply interruption occurs due to operation of a power switch in a power supply device which supplies power to a processor.

In Japanese Patent Application Laid-Open Publication No. 2006-340921, more specifically, a relay as an auxiliary switch is arranged in parallel with a power switch, and a delay circuit which keeps the relay on for a fixed period from when the power switch is turned off operates. Since supply of a commercial voltage into a processor is continued for the fixed time period after the power switch is cut off, a time period t1 required to reliably perform data preservation can be secured.

SUMMARY OF THE INVENTION

A power supply device according to the present invention includes a converter which converts an AC voltage inputted from an external power supply to a DC voltage and outputs the DC voltage, a rectifier circuit which rectifies the AC voltage inputted from the external power supply and outputs a rectified waveform voltage, a voltage cycle detection circuit which detects a voltage cycle in which the rectified waveform voltage reaches a predetermined threshold value and, when the voltage cycle is detected to be longer than a predetermined cycle, outputs a voltage cycle abnormality signal, and power supply cutoff signal output means for outputting a power supply cutoff signal when the voltage cycle abnormality signal is inputted.

BRIEF DESCRIPTION OF THE DRAWINGS

FIG. 8 is a timing chart for explaining operation of the power supply device in FIG. 7.

DETAILED DESCRIPTION OF THE PREFERRED EMBODIMENTS

Embodiments of the present invention will be described below in detail with reference to the drawings.

A technique related to the present invention will be described with reference to FIGS. 7 and 8 before the embodiments of the present invention are described with reference to FIGS. 1 to 6.

Figure 7:
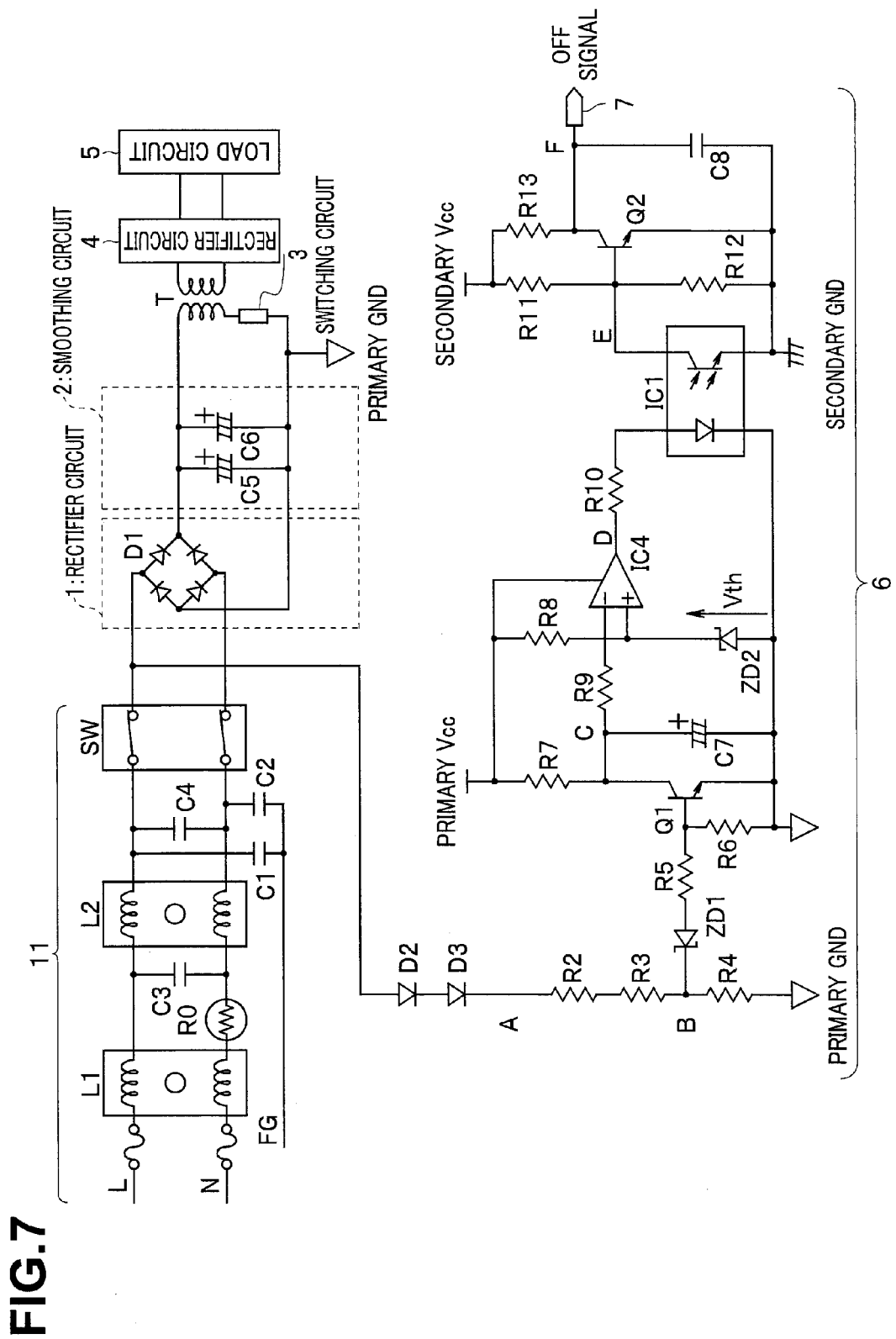
FIG. 7 is a block diagram showing a power supply device according to a technique related to the present invention.

FIG. 7 shows a power supply device according to the technique related to the present invention.

The related technique with a configuration in which a sufficient time period t1 required to preserve data is secured by increasing capacity of smoothing capacitors in a primary circuit of a switching transformer constituting a regulator, in consideration of a power supply interruption due to coming off of an AC cord plug or turning off of a switch in a cart, and the relay and delay circuit described in Japanese Patent Application Laid-Open Publication No. 2006-340921 as the prior art are omitted is shown in FIG. 7. A timing chart when an AC cord plug comes off in the power supply device in FIG. 7 is shown in FIG. 8. Note that, in the following description, a primary side or a primary circuit refers to a primary side of a switching transformer T and a primary side or a primary circuit of a photocoupler IC1 and that a secondary side or a secondary circuit refers to a secondary side of the switching transformer T and a secondary side or a secondary circuit of the photocoupler IC1.

Referring to FIG. 7, reference characters L and N denote respective live-side and neutral-side lines of power lines of a commercial power supply; L1 and L2, common mode filters; R0, a thermistor for rush current limitation; D2 and D3, a diode series circuit for half-wave rectification; C1 to C4, capacitors for high-frequency noise removal; SW, a power switch; and FG, a frame ground connected to ground. Reference numeral 1 denotes a full-wave rectifier circuit which is composed of a diode bridge D1 using four diodes; and 2, a smoothing circuit which is formed by connecting in parallel two smoothing capacitors C5 and C6 which smooth a full-wave rectified output. Reference character T denotes a switching transformer. Reference numeral 3 denotes a switching circuit including a switching element such as a transistor; 4, a rectifier circuit on the secondary side of the switching transformer T; and 5, a load circuit. Reference characters D2 and D3 denote diodes; R2 to R13, resistors; C7, a capacitor for charging; ZD1, a Zener diode (with a Zener voltage Vs) for half-wave rectified voltage input; Q1, an NPN type transistor for half-wave rectified voltage monitoring; ZD2, a Zener diode (with a Zener voltage Vth) for power supply interruption detection; IC4, a comparator for power supply interruption detection; IC1, a photocoupler which optically couples the primary side and the secondary side; Q2, an NPN type transistor for power supply interruption signal (hereinafter referred to as an OFF signal) output; and C8, a capacitor for OFF signal waveform rectification.

FIG. 8 is a timing chart showing operation of the power supply device in FIG. 7. By way of example, FIG. 8 illustrates a case where an AC cord plug comes off at a time P1 when a phase is in a vicinity of 90 degrees (hereinafter abbreviated as deg) in a half-wave rectified voltage waveform to cause a power supply cutoff.

In the timing chart in FIG. 8, reference characters A to D denote signal waveforms of the primary circuit, and a reference point for the waveforms is a primary GND. Reference characters E and F denote signal waveforms of the secondary circuit, and a reference point for the waveforms is a secondary GND.

Operation of the power supply device in FIG. 7 will be described below.

Reference character A denotes a cathode-side potential of the diode D3 that is connected to the line L (live), and the potential is a half-wave rectified voltage with respect to the primary GND. Reference character B denotes an input section of a monitoring circuit 6 for a half-wave rectified voltage from the diodes D2 and D3.

Reference character C denotes a collector output of the transistor Q1 that monitors a half-wave rectified voltage. During a period when the L- or live-to-primary-GND potential is high, a current flows into a base of the transistor Q1 to turn on the transistor Q1. With the operation, the output C becomes low level (hereinafter referred to as LOW level). During a period when the L-to-primary-GND potential is low, the transistor Q1 is turned off, and the capacitor C7 is charged to a voltage of a primary Vcc with a time constant of a time constant circuit (R7 and C7).

Reference character D denotes an output of the comparator IC4 that compares the Zener voltage Vth of the Zener diode ZD2 with a collector voltage denoted by reference character C of the transistor Q1. When the commercial power supply is available, since the capacitor C7 is smoothed at low level, the output D of the comparator IC4 is at high level (hereinafter referred to as HIGH level). When the commercial power supply is stopped, since a charged voltage of the capacitor C7 makes a potential of the output C higher than the threshold value Vth, the output D is at low (LOW) level.

Reference character E denotes an output of the photocoupler IC1. Since the output E is connected to a base of the transistor Q2 whose emitter is grounded, the output E is reverse in voltage level to the output D. Reference character F (OFF signal) denotes an output signal from the monitoring circuit 6. The OFF signal is at HIGH level when the commercial power supply is available and becomes LOW level when the commercial power supply is stopped.

As can be seen from the timing chart waveform in FIG. 8, if an AC cord plug comes off at a time (P1) when the phase is in a vicinity of 90 deg to cause a power supply interruption, the potential of point C is kept at a low level even after the power supply interruption due to residual voltages of the capacitors C1 to C4 upstream of the power switch SW, which results in a longer time period (denoted by reference characters t0 in FIG. 8) from the power supply interruption (P1) to detection of the power supply interruption. The longer time period t0 may interfere with securement of the sufficient time period t1 required to preserve data. This is because a time period for which capacity of the capacitors C5 and C6 of the primary-side smoothing circuit 2 can maintain a secondary output of the transformer T after the power supply interruption P1 is restricted to a sum (=t0+t1) of the time period t0 and the additional time period t1. That is, since a maximum value of t0+t1 is limited by the smoothing capacitor capacity, t1 decreases with increase in t0. Additionally, the power supply device shown in FIG. 7 is based on a design concept of securing the sufficient time period t1 using the smoothing capacitors C5 and C6 of the primary circuit, and the smoothing capacitors need to be designed to be large to some degree in capacity. It is thus difficult to achieve smaller size and lower cost.

As described above, in the power supply device according to the related technique in FIG. 7, the time period t0 shown in FIG. 8 may be long, depending on a time of occurrence of a power supply interruption due to coming off of an AC cord plug (an interruption occurs when the phase is in a vicinity of 90 deg in the example in FIG. 8). Since there are limitations to a time period from a power supply interruption to when the secondary output of the transformer T is stopped, as described above, the time period t1 may be short.

In order to solve the problem, embodiments of the present invention implement:

(a) means for converting a commercial voltage which behaves in an AC manner at 50 to 60 Hz during normal operation to a full-wave rectified waveform;

(b) means for converting zero cross points and vicinities of the full-wave rectified waveform to rectangular pulses at 100 to 120 Hz by using a photocoupler (with a threshold value of VS1) and transmitting the rectangular pulses to a secondary circuit; and (c) means for monitoring the rectangular pulses and, if a level of each rectangular pulse continues to be HIGH or LOW for a fixed period or longer, outputting a power supply interruption signal (OFF signal) to a side of a product circuit (e.g., a processor).

First Embodiment

Figure 1:
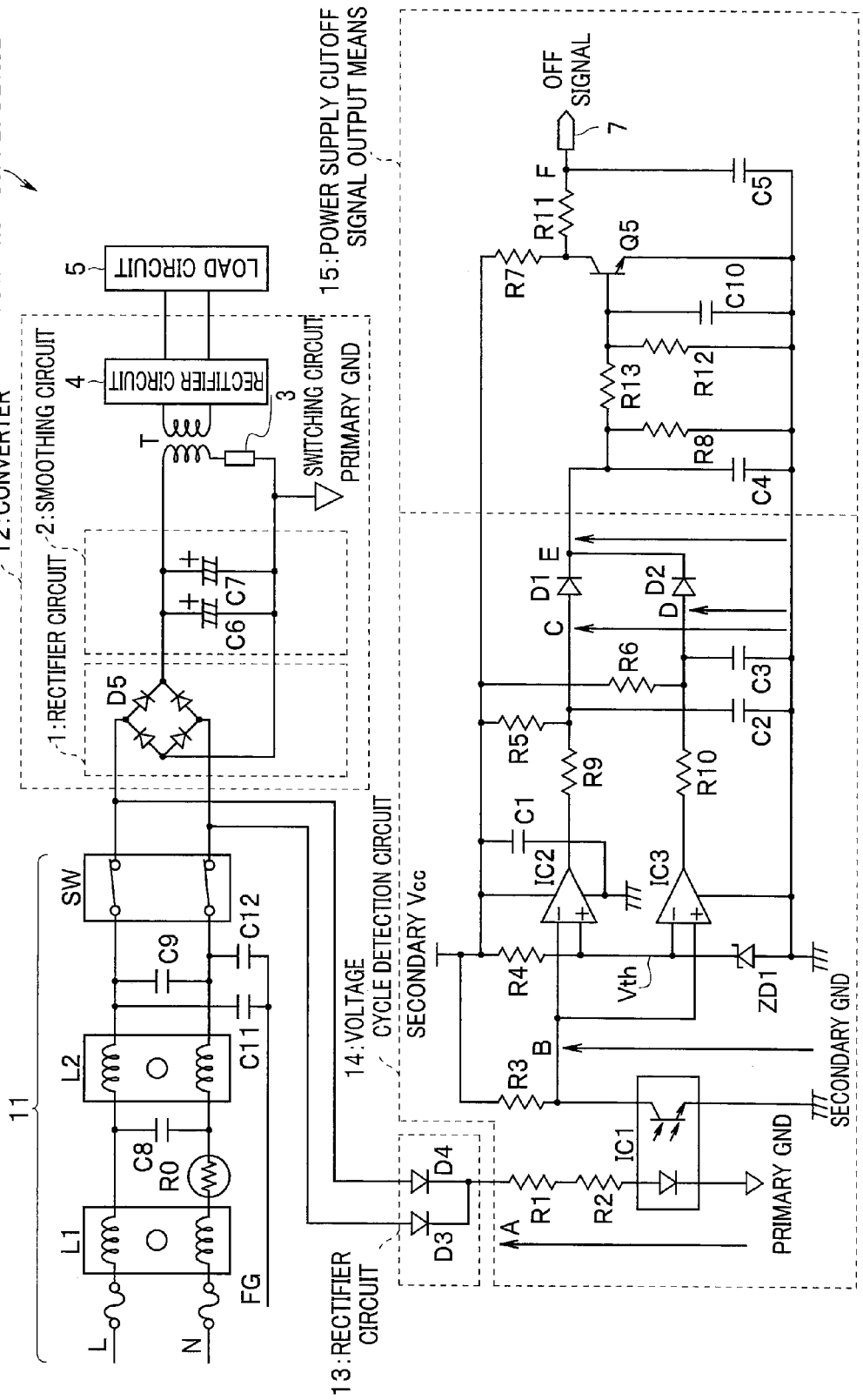
FIG. 1 is a circuit diagram showing a configuration of a power supply device according to a first embodiment of the present invention.

FIG. 1 is a circuit diagram showing a configuration of a power supply device according to a first embodiment of the present invention.

Referring to FIG. 1, a power supply device 10 includes a power input section 11, a converter 12, a rectifier circuit 13, a voltage cycle detection circuit 14, and power supply cutoff signal output means 15.

In the power input section 11, live-side and neutral-side commercial power lines L and N are connected to input terminals of a power switch SW through fuses, a common mode filter L1, a thermistor R0 for rush current limitation, a common mode filter L2, and capacitors C8, C9, C11, and C12 for high-frequency noise removal in order. Respective one ends of the capacitors C11 and C12 of the capacitors C8, C9, C11, and C12 for high-frequency noise removal are connected to the power lines L and N, respectively, and respective other ends of the capacitors C11 and C12 are connected to a frame ground (FG). Respective two ends of each of the capacitors C8 and C9 are connected between the power lines L and N.

The converter 12 is intended to convert an AC voltage inputted from an external commercial AC power supply to a DC voltage and output the DC voltage. The DC voltage obtained by the conversion is supplied to a load circuit 5 such as a processor. The converter 12 includes a rectifier circuit 1 which is composed of a diode bridge D5 and a smoothing circuit 2 which is formed by connecting in parallel two smoothing capacitors C6 and C7. A smoothed DC voltage is converted to AC using a transformer T and a switching circuit 3. After the conversion, a DC voltage at an appropriate voltage level is obtained in a rectifier circuit 4 and is supplied to a product circuit (e.g., a processor) as the load circuit 5.

The rectifier circuit 13 rectifies AC voltages inputted from an external power supply and outputs a rectified waveform voltage. The rectifier circuit 13 is composed of, for example, a full-wave rectifier circuit made up of two diodes D3 and D4 whose cathodes are commonly connected and whose respective anodes are connected to two output lines of the power switch SW.

In the block diagram of FIG. 1, reference character A denotes a full-wave rectified waveform voltage outputted from the rectifier circuit 13. Reference character B denotes a collector output voltage of a phototransistor on a secondary side of a photocoupler IC1 and corresponds to a first signal or a second signal (to be described later). Reference character C denotes an output voltage of a time constant circuit made up of a resistor R5 and a capacitor C2 which are connected to an output end of a comparator IC2 and corresponds to a first confirmation signal (to be described later). Reference character D denotes an output voltage of a time constant circuit made up of a resistor R6 and a capacitor C3 which are connected to an output end of a comparator IC3 and corresponds to a second confirmation signal (to be described later). A confirmation signal here refers to a signal not less than a threshold value of a diode D1 or D2 which is to be detected by the diode D1 or D2.

Reference character E denotes an output voltage of a common connection point of a cathode of the diode D1 and a cathode of the diode D2 and corresponds to a voltage cycle abnormality signal. Reference character F denotes an OFF signal voltage as a collector output voltage of a transistor Q5 which is generated by passing an output voltage of the common output point of the diodes D1 and D2 through the transistor Q5 to reverse the output voltage.

The voltage cycle detection circuit 14 detects a voltage cycle in which the full-wave rectified waveform voltage reaches a predetermined threshold value. If the voltage cycle is detected to be longer than a predetermined cycle, the voltage cycle detection circuit 14 outputs a voltage cycle abnormality signal.

When the full-wave rectified voltage A from the rectifier circuit 13 is inputted to one end of a light-emitting diode on a primary side of the photocoupler IC1 via a series circuit made up of resistors R1 and R2 in the voltage cycle detection circuit 14, if the inputted full-wave rectified voltage is not less than a predetermined threshold value Vs1, the light-emitting diode on the primary side emits light, the phototransistor on the secondary side of the photocoupler IC1 receives the light, and conduction between a collector and an emitter of the phototransistor is provided (the collector and emitter are turned on). At the time, the output B of the photocoupler IC1 serving as a first voltage detector is at a level of a secondary GND, i.e., 0 V as the first signal.

If the inputted full-wave rectified voltage is less than the predetermined threshold value Vs1, the light-emitting diode on the primary side does not emit light, conduction between the collector and the emitter of the phototransistor on the secondary side is not provided, and the collector and emitter are turned off At the time, the output of the photocoupler IC1 serving as a second voltage detector is at a level of a secondary Vcc, i.e., a circuit power supply voltage level as the second signal.

As described above, the photocoupler IC1 functions as the first voltage detector that outputs the first signal when the photocoupler IC1 detects that the full-wave rectified waveform voltage inputted from the rectifier circuit 13 is not less than the predetermined threshold value Vs1 and functions as the second voltage detector that outputs the second signal when the photocoupler IC1 detects that the inputted full-wave rectified waveform voltage is less than the predetermined threshold value Vs1.

More specifically, the photocoupler IC1 receives as input a signal which is obtained by diode ORing of the power lines L and N. The diodes D3 and D4 cause point A to have a full-wave AC voltage waveform. At each zero crossing when a phase of the commercial power supply is in a vicinity of 0 deg or 180 deg, the output of the photocoupler IC1 changes to HIGH and back to LOW. The IC1 output has rectangular pulses with a period of about 10 ms.

Note that the output (point B) of the photocoupler IC1 at the time of a commercial voltage interruption has one of the two possible statuses below. (a) If a power supply interruption occurs when the phase is in a vicinity of 0 deg or 180 deg, the output continues to be HIGH (see FIG. 4). (b) If a power supply interruption occurs when the phase is not in a vicinity of 0 deg or 180 deg, the output continues to be LOW (see FIG. 5). Commercial voltage interruptions are monitored for by monitoring for the operations.

Note that the other end of the light-emitting diode on the primary side of the photocoupler IC1 is connected to a primary-side ground (hereinafter referred to as a primary GND) while the emitter of the phototransistor on the secondary side is connected to a secondary-side ground (hereinafter referred to as a secondary GND).

The collector output B of the phototransistor on the secondary side of the photocoupler IC1 is inputted to a − input end of the comparator IC2 and to a + input end of the comparator IC3. A resistor R4 and a Zener diode ZD1 are connected in series between the secondary Vcc and the secondary GND, and a fixed voltage (Zener voltage) generated in a cathode of the Zener diode ZD1 is supplied as a reference value Vth to a + input end of the comparator IC2 and to a − input end of the comparator IC3. A connection point of a resistor R9 and the resistor R5 is connected to the secondary GND via the capacitor C2. The output end of the capacitor C2 is connected to an anode of the diode D1 via a circuit made up of the resistors R9 and R5 and the capacitor C2, one end of the resistor R5 is connected to the secondary Vcc, and one end of the capacitor C2 is connected to the secondary GND. The output end of the comparator IC3 is connected to an anode of the diode D2 via a circuit made up of resistors R10 and R6 and the capacitor C3, one end of the resistor R6 is connected to the secondary Vcc, and one end of the capacitor C3 is connected to the secondary GND. The resistor R5 and capacitor C2 connected between the secondary Vcc and the secondary GND constitute a time constant circuit. Similarly, the resistor R6 and capacitor C3 connected between the secondary Vcc and the secondary GND also constitute a time constant circuit.

A circuit made up of the comparator IC2, the time constant circuit (R5 and C2), and the diode D1 functions as a first time period detector which outputs the first confirmation signal when the first signal that is the output of the photocoupler IC1 continues to be outputted for a predetermined first time period or longer. A circuit made up of the comparator IC3, the time constant circuit (R6 and C3), and the diode D2 functions as a second time period detector which outputs the second confirmation signal when the second signal that is the output of the photocoupler IC1 continues to be outputted for a predetermined second time period or longer.

The comparator IC2 is a comparator which compares the reference voltage Vth that is generated in the Zener diode ZD1 with the output B of the photocoupler IC1. During a period when the output B of the photocoupler IC1 is lower than the reference voltage Vth, the capacitor C2 is charged to a voltage (a potential of C) of the secondary Vcc with a time constant of the resistor R5 and capacitor C2.

The comparator IC3 is a comparator which compares the reference voltage Vth that is generated in the Zener diode ZD1 with the output B of the photocoupler IC1. During a period when the output B of the photocoupler IC1 is higher than the reference voltage Vth, the capacitor C3 is charged to the voltage (a potential of D) of the secondary Vcc with a time constant of the resistor R6 and capacitor C3.

When either the first confirmation signal or the second confirmation signal is inputted, the voltage cycle detection circuit 14 outputs the voltage cycle abnormality signal as an output (the output E) obtained by ORing of an output of the diode D1 and an output of the diode D2 to the power supply cutoff signal output means 15.

When the voltage cycle abnormality signal is inputted, the power supply cutoff signal output means 15 outputs a power supply cutoff signal (OFF signal).

Figures 2, 3:
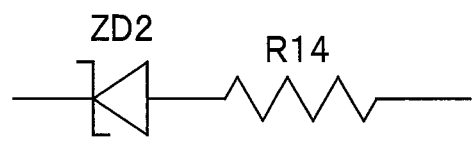
FIG. 2 is a circuit diagram showing a different configuration example which can be used instead of a resistive element as a part of a power supply cutoff signal (OFF signal) output section in FIG. 1.
FIG. 3 is a chart showing a truth table of a NOR circuit whose input ends are point C and point D in FIG. 1.

In the power supply cutoff signal output means 15, a capacitor C4 is connected between common connection point E of the diodes D1 and D2 and the secondary GND, and a resistor R8 is connected between common connection point E and the secondary GND. Common connection point E is connected to a base of the NPN type transistor Q5 via a resistor R13, the base of the transistor Q5 is connected to the secondary GND via a resistor R12, an emitter of the transistor Q5 is directly connected to the secondary GND, and a collector of the transistor Q5 is connected to the secondary Vcc via a resistor R7. A bypass capacitor C10 for noise removal is connected between the base of the transistor Q5 and the secondary GND. Note that a series circuit as shown in FIG. 2 which is made up of a Zener diode ZD2 and a resistor R14 may be used instead of the resistor R13.

The collector of the transistor Q5 is connected to connection point F that outputs the OFF signal via a resistor R11. Connection point F is connected to the secondary GND via a capacitor C5 and is connected to an output terminal 7 which outputs the OFF signal.

The NPN type transistor Q5 is a grounded-emitter circuit which receives as input an output signal obtained by diode ORing of the diodes D1 and D2. The transistor Q5 constitutes a NOR circuit whose inputs are point C and point D (see the truth table in FIG. 3). The OFF signal has a high level voltage when there is a supplied voltage from the commercial power supply and has a low level voltage when supply of voltage from the commercial power supply is interrupted, and there is no supplied voltage.

A voltage supplied to the base of the transistor Q5 is a voltage which is obtained by dividing a voltage at common connection point E, i.e., a charged voltage to which the capacitor C4 is charged by the resistors R13 and R12. Accordingly, in a process in which the capacitor C4 is charged, when the divided voltage of a connection point of the resistor R13 and the resistor R12 exceeds a base-to-emitter voltage (=a threshold value VS2) of the transistor Q5, the transistor Q5 is brought into conduction (turned on), and the OFF signal from the output terminal 7 has a low level voltage. At the time point, an interruption of the commercial power supply is detected. By using the OFF signal at low level, supply of power to an image pickup device and a display device (not shown) inside a medical device can be shut off.

As regards a secondary output from the rectifier circuit 4 on the secondary side of the converter 12, even when the OFF signal is at low level, a sufficient output-maintained time period t1 for the secondary output can be secured by increasing smoothing capacitor capacity of the primary-side smoothing circuit 2 using the capacitors C6 and C7. Even in the event of a power supply interruption due to coming off of an AC cord plug or turning off of a switch in a cart, data preservation can be reliably performed.

Figure 4:
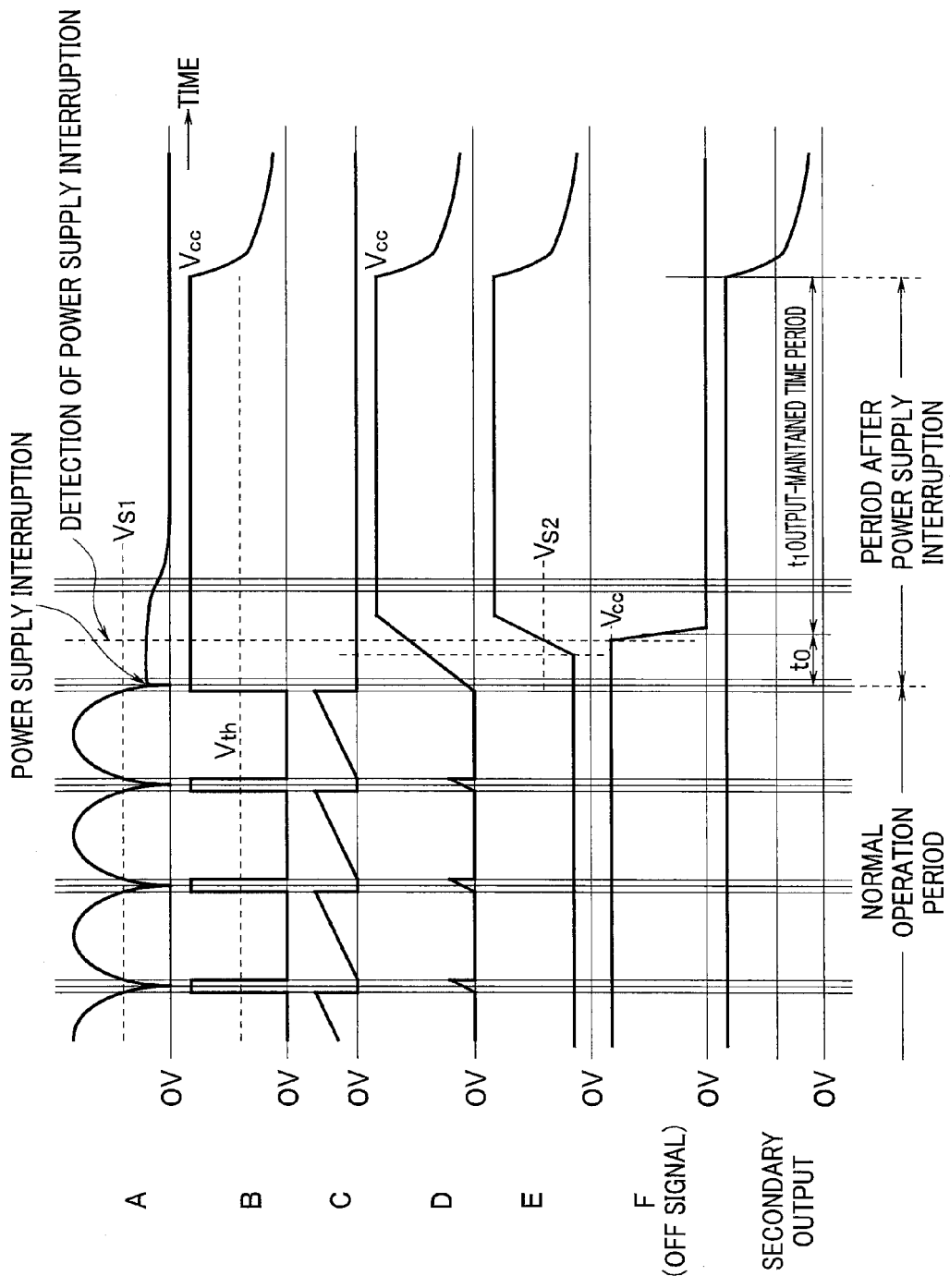
FIG. 4 is a timing chart for explaining an example of operation when supply of power to the power supply device in FIG. 1 is interrupted.
Figure 5:
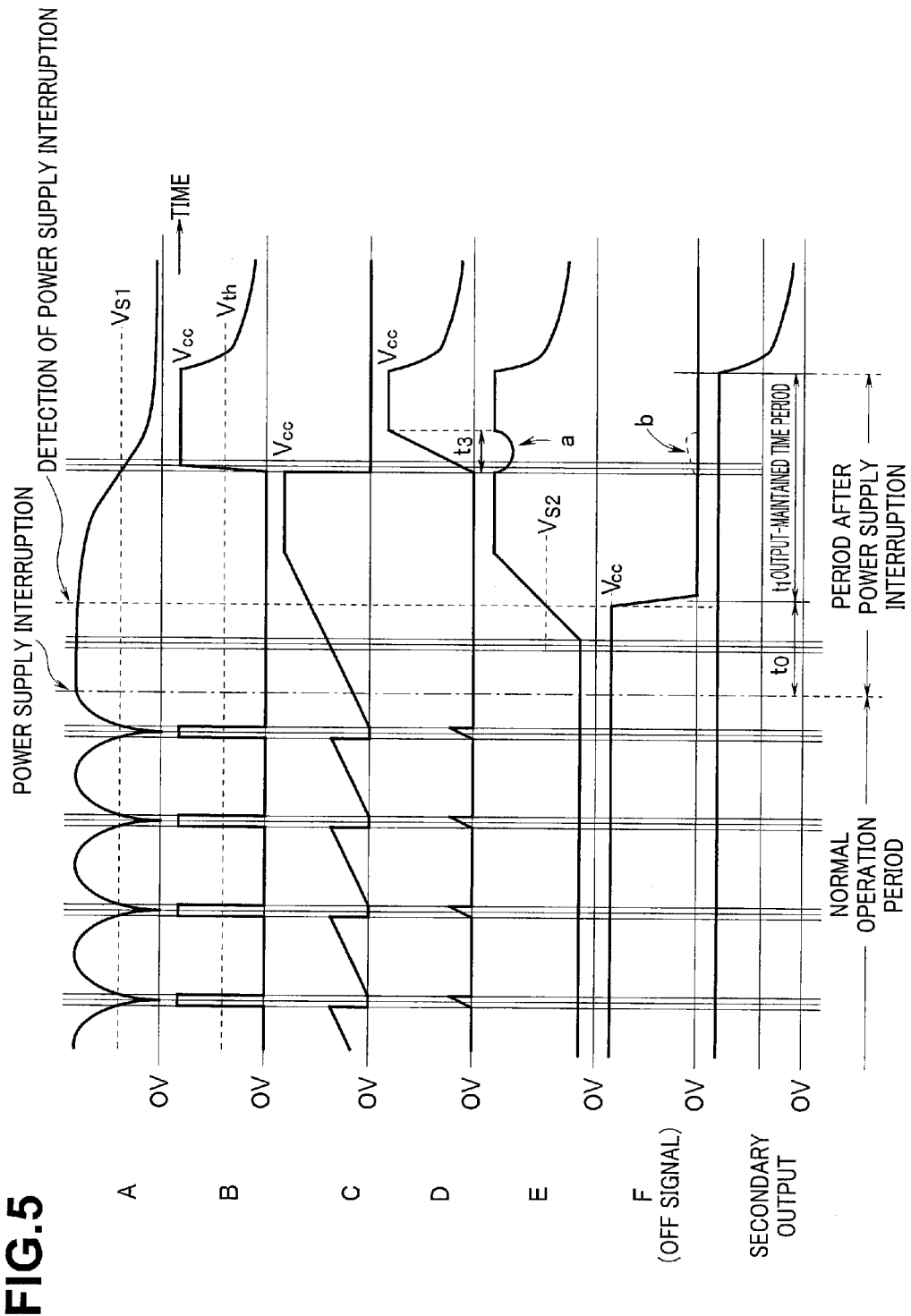
FIG. 5 is a timing chart for explaining another example of operation when supply of power to the power supply device in FIG. 1 is interrupted.

As can be seen from the timing charts in FIGS. 4 and 5, a time period t0 is not determined due to residual voltages of the capacitors C8, C9, C11, and C12 but determined by passing the full-wave rectified waveform voltage through the photocoupler and monitoring the secondary-side voltage of the photocoupler. Since the time period t0 is not affected by the residual voltages of the capacitors C8, C9, C11, and C12, the time period t0 can be shortened.

The timing charts in FIGS. 4 and 5 will be described.

FIGS. 4 and 5 each show voltage waveforms at respective points A to F in the circuit diagram when an unexpected "power supply interruption" due to, e.g., coming off of an AC cord plug occurs upstream of the power switch SW while the power supply device 10 is operating normally.

Reference character A denotes a signal waveform of a primary circuit, and a reference point for the waveform is the primary GND. Reference characters B to F denote signal waveforms of a secondary circuit, and a reference point for the waveforms is the secondary GND.

FIG. 4 shows voltage waveforms at respective points A to F when a power supply interruption due to, e.g., coming off of an AC cord plug occurs at a time when a phase of an inputted AC power supply voltage is in a vicinity of 0 deg or 180 deg while the power supply device 10 is operating normally.

FIG. 5 shows voltage waveforms at respective points A to F when a power supply interruption due to, e.g., coming off of an AC cord plug occurs at a time when the phase of the inputted AC power supply voltage is not in a vicinity of 0 deg or 180 deg (e.g., when the phase is in a vicinity of 90 deg, or the like).

In FIG. 4, a power supply interruption occurs when a phase of the full-wave rectified waveform voltage A from the rectifier circuit 13 is in a vicinity of 0 deg or 180 deg. After the power supply interruption, a primary-side voltage of the photocoupler IC1 is maintained below the threshold value VS1 of the photocoupler IC1, and the photocoupler IC1 is brought out of conduction (turned off). The secondary-side output voltage B of the photocoupler IC1 is maintained at HIGH level based on the secondary Vcc. The state is continued for a time period (=t0+t1) which is determined by capacity of the smoothing capacitors C6 and C7 of the primary smoothing circuit 2.

After the power supply interruption, since the photocoupler IC1 is maintained off, and the secondary-side output voltage B of the photocoupler IC1 is maintained at HIGH level, a comparison output of the comparator IC2 (with the threshold value Vth) is at LOW level, and the input voltage C of the diode D1 is also at LOW level.

At the time, an output of the capacitor C3 which is a comparison output of the comparator IC3 (with the threshold value Vth) climbs with the time constant of the resistor R6 and capacitor C3 and is maintained at a voltage which has climbed to the voltage of the secondary Vcc at HIGH level. The input voltage D of the diode D2 is at HIGH level.

As a result, the ORed output voltage E of the diodes D1 and D2 has substantially a same voltage waveform as the voltage D though the voltage E rises slightly slowly due to capacity of the capacitor C4. The voltage E, i.e., a voltage of the capacitor C4 is applied across a series circuit made up of the resistors R13 and R12. In a process in which the voltage E rises, at a time point when a potential of the connection point of the resistors R13 and R12, i.e., a base potential of the transistor Q5 becomes not less than a base-to-emitter conduction (ON) potential (=the threshold value VS2) of the transistor Q5, the transistor Q5 is turned on, and the OFF signal outputted to output terminal F changes from HIGH level to LOW level. With the OFF signal at LOW level, a driving power supply for a device other than the load circuit 5 (e.g., a processor), such as an image pickup device or a display device, can be stopped.

As described above, even if the OFF signal becomes LOW level, electric charge accumulated in the smoothing capacitors of the primary-side smoothing circuit 2 allows the secondary output at high level to be continuously supplied to the load circuit 5 on the secondary side for the output-maintained time period t1.

In FIG. 5, since a power supply interruption occurs when the phase of the full-wave rectified waveform voltage A from the rectifier circuit 13 is not in a vicinity of 0 deg or 180 deg (e.g., when the phase is in a vicinity of 90 deg), i.e., in a vicinity of a peak of the full-wave rectified waveform voltage A, the residual voltages of the capacitors C8, C9, C11, and C12 inside the power input section 11 are maintained at high level, and the full-wave rectified waveform voltage A remains above the threshold value VS1 of the photocoupler IC1 for some time. After that, the primary-side voltage A of the photocoupler IC1 declines gradually with decline in the residual voltages. When the primary-side voltage A drops below the threshold value VS1, the photocoupler IC1 is brought out of conduction (turned off), and the secondary-side output voltage B of the photocoupler IC1 becomes HIGH level. After the change, the voltage B is maintained at HIGH level until passage of a time period corresponding to the output-maintained time period t1 based on the capacity of the capacitors C6 and C7 of the primary-side smoothing circuit 2.

The secondary-side output voltage B of the photocoupler IC1 is maintained at LOW level for a relatively long fixed period after the power supply interruption is detected after the power supply interruption. Accordingly, an output of the capacitor C2 which is the comparison output of the comparator IC2 (with the threshold value Vth) climbs with the time constant of the resistor R5 and capacitor C2, and the input voltage C of the diode D1 is maintained at a voltage which has climbed to the voltage of the secondary Vcc at HIGH level.

At the time, the comparison output of the comparator IC3 (with the threshold value Vth) remains at LOW level for the fixed period, and the input voltage D of the diode D2 is at LOW level after the power supply interruption.

The secondary-side output voltage B of the photocoupler IC1 after the photocoupler IC1 is turned off is maintained at the voltage of the secondary Vcc until passage of the time period t1. When the voltage B changes to HIGH level, the comparison output of the comparator IC2 becomes LOW level, the input voltage C of the diode D1 becomes LOW level, and the input voltage D of the diode D2 rises from LOW level to HIGH level and is outputted.

The voltage E of the common output point of the two diodes D1 and D2 is as indicated by E in FIG. 5. Although the voltage E is originally an ORed voltage of the voltage C and the voltage D, the voltage C is a sawtooth waveform voltage with cycles having a power half-period before the power supply interruption. Since the voltage C charges the capacitor C4 through the diode D1, the voltage E is smoothed to be a DC voltage at low level before the power supply interruption. In the case of FIG. 5, the power supply interruption occurs in a vicinity of a peak of the full-wave rectified voltage A. As a result, the output voltage B of the photocoupler IC1 is at LOW level, and the voltage C at HIGH level on the output side of the comparator IC2 climbs gradually with the time constant of the resistor R5 and capacitor C2 to reach the voltage of the secondary Vcc at HIGH level. When the full-wave rectified voltage A drops below the threshold value VS1 of the photocoupler IC1, the voltage C declines to LOW level.

As for change in the input voltage C over time of the diode D1, the gradually-climbing voltage C in a vicinity of the time of the power supply interruption continues to charge the capacitor C4 through the diode D1 and be smoothed as before the power supply interruption. As a result, the voltage E is maintained to be the DC voltage at low level for a short period immediately after the power supply interruption. After the maintenance, the voltage E starts to climb around a time point when the voltage C reaches a fixed voltage (at HIGH level) of the Vcc. The voltage D is a waveform voltage which climbs gradually from a time when the secondary voltage B of the photocoupler IC1 becomes HIGH level to reach the voltage of the Vcc. The voltage D and the voltage C are combined in the capacitor C4, which results in the waveform as indicated by E in FIG. 5.

As described above, the voltage E is divided by the resistors R13 and R12, and the divided voltage is applied to the base of the transistor Q5. In a process in which the voltage E climbs, when the voltage E exceeds the base-to-emitter ON voltage of the transistor Q5, the transistor Q5 is turned on, and the OFF signal at point F becomes LOW level.

A waveform of the combined voltage E at output point E of the diodes D1 and D2 and a waveform of the output voltage F at point F, i.e., the OFF signal which are shown in FIG. 5 have disordered waveform portions, such as a portion a in the waveform of the voltage E and a portion b in the waveform of the voltage F. In order to prevent generation of such portions, the capacitors C4 and C5 are provided. The portions a and b will be described below.

As in FIG. 5, when an input voltage at point A of the photocoupler IC1 declines to a certain voltage with reduction in the residual voltages of the capacitors C8, C9, C11, and C12 through discharging after the OFF signal denoted by reference character F switches from HIGH level (=the secondary Vcc) to LOW level (=0 V), the photocoupler IC1 is turned off, which changes the output (point B) of the photocoupler IC1 to HIGH level. At the time, a phenomenon in which the OFF signal switches sharply from LOW level to HIGH level may occur. In order to prevent the phenomenon, the capacitors C4 and C5 are mounted.

(a) A discharge time period corresponding to the portion a in the waveform of the ORed output (the output at point E) of the diodes D1 and D2 is lengthened by increasing the capacity of the capacitor C4. That is, presence of the capacitor C4 makes the discharge time period longer and prevents a sharp fall. A length t3 of time corresponding to the recessed portion a will be referred to as a third time period.

(b) The portion b (a dotted portion in FIG. 5) in the waveform of the OFF signal at point F is prevented from rising sharply by increasing capacity of the capacitor C5. That is, presence of the capacitor C5 prevents a sharp rise in the OFF signal. The configuration allows retainment of waveform quality of the OFF signal, i.e., maintenance of LOW level state and prevents the OFF signal from changing momentarily to HIGH level to cause a change in output-maintained state of the converter secondary output used for data preservation. Accordingly, the power supply cutoff signal output means 15 includes signal retention means for retaining output state of the power supply cutoff signal (OFF signal) at least for the third time period.

In the present embodiment, a new solution for ensuring data preservation is to convert a commercial power supply voltage to a full-wave rectified voltage and monitor intervals between zero cross points (at 100 to 120 Hz). If an interval between zero cross points is less than a fixed time period, it is determined that normal operation is being performed. On the other hand, if the interval is not less than the fixed time period, it is determined that power supply is interrupted, and a power supply interruption signal (OFF signal) is outputted to a side of a product circuit such as a processor.

In the case of the present embodiment, since a power supply interruption can be quickly sensed without being affected by residual voltages, even in the event of a power supply interruption due to coming off of an AC cord plug or turning off of a switch in a cart, a time period to maintain a secondary output power supply required for data preservation can be secured. Additionally, lower capacity of smoothing capacitors of a primary circuit and omission of a relay can be achieved, and smaller size and price reduction of a power supply unit can thus be expected.

According to the first embodiment, since a power supply interruption can be quickly sensed without being affected by residual voltages, the time period t0 is short. Even in the event of a power supply interruption due to coming off of an AC cord plug or turning off of a switch in a cart, the time period t1 to maintain a secondary output voltage required for data preservation and a patient circuit power supply can be secured. Accordingly, data preservation can be reliably performed, and lower capacity of smoothing capacitors of a primary circuit and omission of a relay can be achieved. Smaller size and price reduction of a power supply unit can also be achieved.

Second Embodiment

Figure 6:
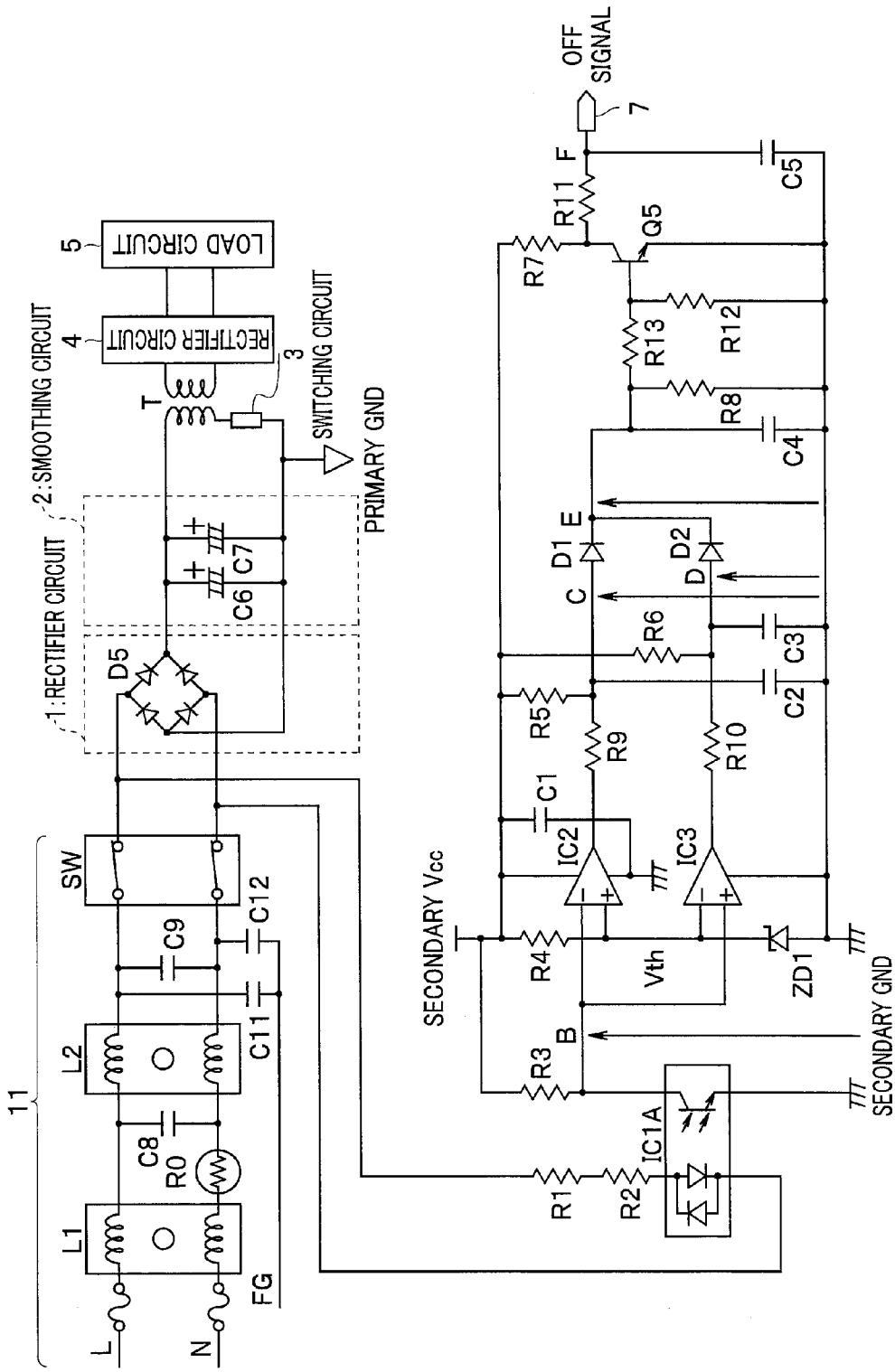
FIG. 6 is a circuit diagram showing a configuration of a power supply device according to a second embodiment of the present invention.

FIG. 6 is a circuit diagram showing a configuration of a power supply device according to a second embodiment of the present invention.

The embodiment in FIG. 6 shows a configuration example in which a photocoupler IC1A for AC is used instead of the photocoupler IC1 for generating a signal at point B according to the embodiment in FIG. 1. Other components are same as in FIG. 1.

The use of a photocoupler for AC allows omission of the diodes D3 and D4 in FIG. 1 and can achieve reduction in the number of parts.

As the photocoupler IC1A for AC, for example, PS2505-1, PS2505-4, PS2505L-1, or PS2505L-4 which is an AC input response type photocoupler available from Renesas Electronics Corporation can be used.

According to the second embodiment, the number of parts of a power supply device can be reduced.

Note that the present invention is not limited to the above-described embodiments and that various changes, modifications, and the like can be made without departing from scope of the present invention. Various inventions can be made by appropriately combining a plurality of constituent elements disclosed in the above embodiments.

What is claimed is:

1. A power supply device comprising:
   a converter which converts an AC voltage inputted from an external power supply to a DC voltage and outputs the DC voltage;
   a full-wave rectifier circuit which rectifies the AC voltage inputted from the external power supply and outputs a full-wave rectified waveform voltage;
   a voltage cycle detection circuit which detects a voltage cycle in which the full-wave rectified waveform voltage reaches a predetermined threshold value and, when the voltage cycle is detected to be longer than a predetermined cycle, outputs a voltage cycle abnormality signal; and
   power supply cutoff signal output means for outputting a power supply cutoff signal when the voltage cycle abnormality signal is inputted,
   wherein the voltage cycle detection circuit includes:
      a first voltage detector which outputs a first signal when the full-wave rectified waveform voltage of the full-wave rectifier circuit is detected to be not less than the predetermined threshold value,
      a first time period detector which outputs a first confirmation signal when the first signal continues to be outputted for a predetermined first time period or longer,
      a second voltage detector which outputs a second signal when the full-wave rectified waveform voltage of the full-wave rectifier circuit is detected to be less than the predetermined threshold value, and
      a second time period detector which outputs a second confirmation signal when the second signal continues to be outputted for a predetermined second time period or longer and outputs the voltage cycle abnormality signal when one of the first confirmation signal and the second confirmation signal is inputted.

2. The power supply device according to claim 1, wherein the power supply cutoff signal output means includes signal retention means for retaining an output of the power supply cutoff signal at least during a third time period starting from when the full-wave rectified waveform voltage is detected to be less than the predetermined threshold value.

* * * * *